United States Patent
Lee-Chen et al.

(10) Patent No.: US 9,463,197 B2
(45) Date of Patent: Oct. 11, 2016

(54) METHOD FOR TREATING ABNORMAL POLYGLUTAMINE-MEDIATED DISEASE

(71) Applicant: NATIONAL TAIWAN NORMAL UNIVERSITY, Taipei (TW)

(72) Inventors: Guey-Jen Lee-Chen, Taipei (TW); Hsiu-Mei Hsieh, Taipei (TW); Guan-Chiun Lee, Taipei (TW)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 6 days.

(21) Appl. No.: 14/331,613

(22) Filed: Jul. 15, 2014

(65) Prior Publication Data
US 2015/0025028 A1    Jan. 22, 2015

(30) Foreign Application Priority Data

Jul. 17, 2013  (TW) .............................. 102125534 A

(51) Int. Cl.
*A01N 43/04* (2006.01)
*A61K 31/715* (2006.01)
*A61K 31/7016* (2006.01)
*A61K 45/06* (2006.01)

(52) U.S. Cl.
CPC ........... *A61K 31/7016* (2013.01); *A61K 45/06* (2013.01)

(58) Field of Classification Search
None
See application file for complete search history.

(56) References Cited

PUBLICATIONS

Tanaka et al. J. Mol. Med. (2005), vol. 83, pp. 343-352.*
Goddijn et al. Plant Physiol. (1997), vol. 113, pp. 181-190.*
Luyckx et al. Clinical Ophthalmology (2011), vol. 5, pp. 577-581.*
Seki et al. Journal of Biological Chemistry (2010), vol. 285, No. 43, pp. 33252-33264.*
Underwood et al. The Cerebellum (2008), pp. 215-221.*
Motomasa Tanaka et al., "Trehalose alleviates polyglutamine-mediated pathology in a mouse model of Huntington disease", Nature Medicine, vol. 10, No. 2, Feb. 2004, pp. 148-154.

* cited by examiner

*Primary Examiner* — Patrick Lewis
(74) *Attorney, Agent, or Firm* — Bacon & Thomas, PLLC

(57) ABSTRACT

A method for treating an abnormal polyglutamine-mediated disease is disclosed, which comprises: administering a pharmaceutical composition comprising a trehalose-based compound to a subject in need. Additionally, the pharmaceutical composition optionally further comprises a trehalase inhibitor.

7 Claims, 10 Drawing Sheets

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial sequence
<220> FEATURE:
<223> OTHER INFORMATION: Synthesized primer

<400> SEQUENCE: 1
attcagctaa gtatgcaagg tagttcca                                          28

<210> SEQ ID NO 2
<211> LENGTH: 30
<212> TYPE: DNA
<213> ORGANISM: Artificial sequence
<220> FEATURE:
<223> OTHER INFORMATION: Synthesized primer

<400> SEQUENCE: 2
catgccatgg catgtttttt tccttctgtt                                        30

<210> SEQ ID NO 3
<211> LENGTH: 23
<212> TYPE: DNA
<213> ORGANISM: Artificial sequence
<220> FEATURE:
<223> OTHER INFORMATION: Synthesized primer

<400> SEQUENCE: 3
aagcttccat gccgtcggag aag                                               23

<210> SEQ ID NO 4
<211> LENGTH: 21
<212> TYPE: DNA
<213> ORGANISM: Artificial sequence
<220> FEATURE:
<223> OTHER INFORMATION: Synthesized primer

<400> SEQUENCE: 4
ttttacactg acaatttcat c                                                 21
```

METHOD FOR TREATING ABNORMAL POLYGLUTAMINE-MEDIATED DISEASE

CROSS REFERENCE TO RELATED APPLICATION

This application claims the benefits of the Taiwan Patent Application Serial Number 102125534, filed on Jul. 17, 2013, the subject matter of which is incorporated herein by reference.

BACKGROUND OF THE INVENTION

1. Field of the Invention

The present invention related to a method for treating abnormal polyglutamine (polyQ)-mediated disease with a pharmaceutical composition comprising trehalose-based compound, which can enhance autophagy activity to achieve the purpose of suppressing aggregation of polyglutamine in a subject in need.

2. Description of Related Art

The spinocerebellar atrophy is referred as spinocerebellar ataxias (SCAs), which is a complex group of heterogeneous autosomal dominant neurodegenerative disorder. Spinocerebellar ataxias (SCAs), caused by expanded CAG repeats encoding a long polyQ tract in mutant proteins, and the misfolded polyQ proteins accumulate in the nucleus and cytoplasm of neural cells. The clinical symptom of spinocerebellar atrophy comprises cerebellar degeneration, dysfunctions of nervous system and other parts.

On the current market, there is no drug for curing or suppressing polyglutamine related spinocerebellar ataxia progression, and the symptom thereof is irreversible: patients may fail to appropriately control their movements at the beginning; with the deterioration of disease condition, patients become failing to walk and write progressively, and finally become failing to talk and swallow. In the worst case, it may bring patients to an end with death. However, even though there is atrophy of the cerebellum, the brainstem, and the spinal cord, the intelligence is completely unaffected, so that patients can be clearly conscious of the fact that their bodies gradually become inactive.

In view of the gradually increased global population suffering from cerebellar atrophy, what is needed is to find a compound capable of reducing the accumulation of polyglutamine to be used for the manufacture of pharmaceutical compositions for abnormal accumulated polyglutamine-mediated diseases, to serve as an adjuvant therapy for neurodegenerative disease, such as cerebellar atrophy, thereby effectively slowing down the disease progression, as well as providing the patients with a better quality of life.

SUMMARY OF THE INVENTION

An object of the present invention is to provide a method for treating an abnormal polyglutamine-mediated disease to give assistance to the treatment of spinocerebellar ataxia.

Another object of the present invention is to provide a method for enhancing autophagy activity to achieve the purpose of suppressing aggregation of polyglutamine in a subject in need.

To achieve the object, the present invention provides a pharmaceutical composition for treating an abnormal polyglutamine-mediated disease, which comprises: at least one trehalose-based compound selected from a group consisting of a compound of the following formula 1, a compound of the following formula 2, a compound of the following formula 3, and derivatives thereof.

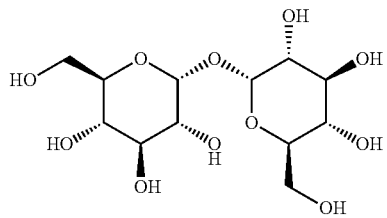

[Formula 1]

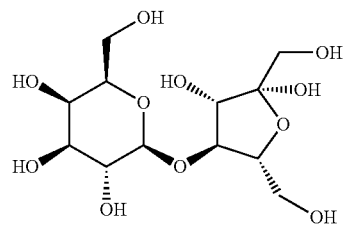

[Formula 2]

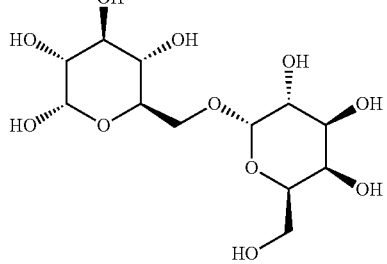

[Formula 3]

In the abnormal polyglutamine-mediated disease, the expanded polyglutamine tracts in respective proteins lead to protein misfolding and subsequent aggregation, and the clearance of the misfolding and aggregated proteins via the autophagy pathways is suppressed. Hence, the aforementioned compound represented by the formula 1, 2 or 3 can enhance the autophagy activity to solve the aforementioned problems.

It should be noted that the derivatives of the aforementioned compound represented by the formula 1, 2 or 3 may also have the same efficacy. The examples of the derivatives thereof, which can be obtained through any chemical modification generally used in the art, may comprise: an amino sugar with an amino group; a deoxy sugar with a hydrogen group; a phosphor sugar with a phosphate group; an acidic sugar with a carboxyl group (—COOH); and derivatives with functional groups such as $C_{1-10}$ linear or branch alkyl, $C_{2-10}$ linear or branch alkenyl, $C_{2-10}$ linear or branch alkynyl, $C_{3-12}$ cycloalkyl, $C_{3-12}$ cycloalkenyl, and $C_6$, $C_{10}$ or $C_{14}$ aryl, which substitutes the —OH group(s) thereon. However, the derivatives of the present invention are not limited thereto, and any other derivative with suitable modifications, which a person skilled in the art can refer to, can be used herein.

In the present invention, the type of the abnormal polyglutamine-mediated disease is not particularly limited. Preferably, the abnormal polyglutamine-mediated disease is spinocerebellar ataxia. In spinocerebellar ataxia, the expansions of CAG trinucleotide repeats encoding a polyglutamine stretch have been shown to cause dominantly inherited SCA1, SCA2, SCA3, SCA6, SCA7, SCA8, SCA17 and dentatorubropallidoluysian atrophy (DRPLA). These polyQ-mediated genetic disorders in SCAs have shown selective progressive degeneration of the cerebellum, brainstem, and spinal cord tract, with prominent pathological hallmark of intranuclear and cytoplasmic accumulation of aggregated polyQ proteins inside degenerated neurons, thereby causing the dysfunction and degeneration of specific neurons.

In addition, the used concentration of the aforementioned compound represented by the formula 1, 2 or 3 is not particularly limited, and can be adjusted according to actual situation for use, such as the severity of the diseases or used complementary drugs. In a preferred embodiment of the present invention, the concentration of the trehalose-based compound is preferably in a range from 50 nM to 200 µM, and more preferably in a range from 100 nM to 100 µM, based on a total weight of the pharmaceutical composition.

The pharmaceutical composition of the present invention may further comprise a trehalase inhibitor. It can inhibit the activity of the trehalase to prevent trehalose from being degraded. In addition, the pharmaceutical composition containing the trehalase inhibitor can further decrease the accumulation of aggregated polyQ proteins. Herein, the sort of the trehalase inhibitor is not particularly limited, and can be any trehalase inhibitor generally known in the art, such as validamycin A, validoxylamine A, trehazolin, MDL 25637, castanospermine, deoxynojirimycin, 1-thiatrehazolin, salbostatin and calystegin B4.

In the present invention, the aforementioned compound represented by the formula 1, 2 or 3 can enhance the autophagy activity, which may be accomplished by increasing the expression of autophagosomes and a ratio of LC3-II (light-chain 3 protein-II) to LC3-I (light-chain 3 protein-I) (LC3-II/LC3-I).

Hence, the present invention further provides a method for treating an abnormal polyglutamine-mediated disease, which comprises: administering a pharmaceutical composition comprising at least one trehalose-based compound represented by the formula 1, 2 or 3 to a subject in need. Additionally, the present invention also provides a method for enhancing autophagy activity, which comprises: administering a pharmaceutical composition comprising at least one trehalose-based compound represented by the formula 1, 2 or 3 to a subject in need.

The term "inhibit", "reduce" or "decrease" used herein refers to the case that the pharmaceutical composition including the trehalose-based compound represented by the formula 1, 2 or 3 of the present invention is applied to a subject suffering from abnormal polyglutamine-mediated disease (such as spinocerebellar ataxia), having symptom of abnormal polyglutamine-mediated disease, or having a tendency of development of abnormal polyglutamine-mediated disease, in order to achieve the treatment, mitigation, slowing, therapy, improvement, or recovery of the tendency of the disease and symptoms.

To implement the method according to the present invention, the above pharmaceutical composition can be administered via oral administering, parenteral administering, inhalation spray administering, topical administering, rectal administering, nasal administering, sublingual administering, vaginal administering, or implanted reservoir, and so on. The term "parenteral" used here refers to subcutaneous injection, intradermal injection, intravenous injection, intramuscular injection, intraarticular injection, intraarterial injection, joint fluid injection, intrathoracic injection, intrathecal injection, injection at morbid site, and intracranial injection or injection technique.

Hence, the pharmaceutical composition containing the aforementioned compound can be formulated into health foods or clinical drugs for preventing and treating abnormal polyglutamine-mediated diseases through any medicine manufacturing procedure. According to the requirement for use, the pharmaceutical composition of the present invention may further comprise at least one of a pharmaceutically acceptable carrier, a diluent, or an excipient in the art. For example, the aforementioned compound is encapsulated into liposome to facilitate delivery and absorption; the aforementioned compound is diluted with aqueous suspension, dispersion or solution to facilitate injection; or the aforementioned compound is prepared in a form of a capsule or tablet for storage and carrying.

More specifically, the pharmaceutical composition of the present invention can be formulated into a solid form or a liquid form. The solid dosage formulations may comprise: powders, pellets, tablets, capsules, and suppositories, but the present invention is not limited thereto. In addition, excipients, flavoring agents, preservatives, disintegrants, flow aids, and fillers may be comprised in the solid dosage formulation, but the present invention is not limited thereto. The liquid dosage formulations may comprise: water, solution (such as propylene glycol solution), suspension, and emulsifier; and suitable coloring agents, flavoring agents, stabilizers and thickening agents may also be used to prepare the liquid dosage formulations.

For example, the powder formulation can be prepared by mixing the compound of the present invention with a suitable pharmaceutical acceptable excipient (such as sucrose, starch and microcrystalline cellulose). The pellet formulation can be prepared by mixing the compound of the present invention with a suitable pharmaceutical acceptable excipient and a suitable pharmaceutical acceptable binder (such as polyvinyl pyrrolidone and hydroxypropyl cellulose), followed by wet granulation with a solvent (such as water, alcohol and isopropanol) or dry granulation with pressure. In addition, the tablet formulation can be prepared by mixing the pellet formulation with a suitable pharmaceutical acceptable flow aids (such as magnesium stearate), followed by pressing with a tablet press machine. Therefore, the administered formulations can be selected according to the subject's requirement.

Other objects, advantages, and novel features of the invention will become more apparent from the following detailed description when taken in conjunction with the accompanying drawings.

DETAILED DESCRIPTION OF THE PREFERRED EMBODIMENT

[Trehalose and Analogs]

Figure 1:
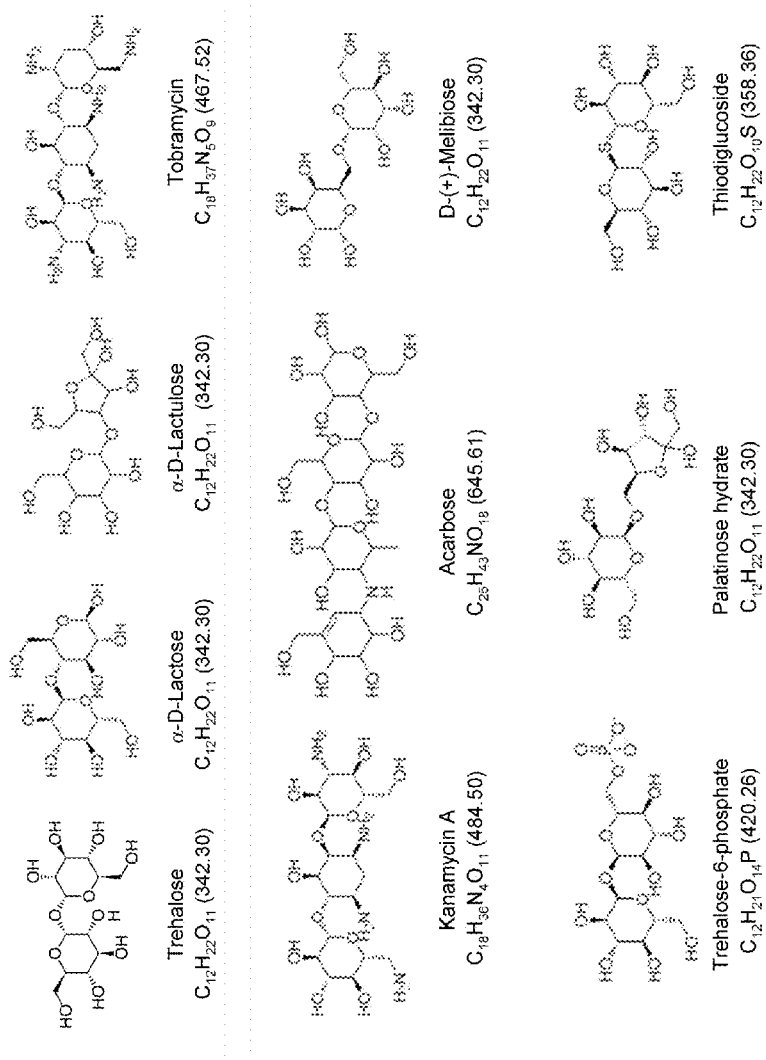
FIG. 1 shows structures, formulas, and molecular weights of the trehalose and analogs used in one preferred embodiment of the present invention.

We searched trehalose analogs from the ZINC compound database (http://zinc.docking.org/) based on compound topology and function group analyses; and obtained the human trehalase structure with a homology-modeling server. In addition, we used our in-house docking tool, GEMDOCK to discover inhibitors and binding sites for several targets. After the docking procedure, iGEMDOCK was used to screen those with similar hydrogen bonding network to trehalose. A total of 17,833,934 compounds including FDA drugs and natural products were examined, 21 were selected and 9 available were obtained. The 9 commercial available compounds are shown in FIG. 1, which are respectively trehalose ($C_{12}H_{22}O_{11}$, MW 342.30), α-D-lactose ($C_{12}H_{22}O_{11}$, MW 342.30), α-D-lactulose ($C_{12}H_{22}O_{11}$, MW 342.30), tobramycin ($C_{18}H_{37}N_5O_9$, MW 467.52), kanamycin A ($C_{18}H_{36}N_4O_{11}$, MW 484.50), acarbose ($C_{25}H_{43}NO_{18}$, MW 645.61), D-(+)-melibiose ($C_{12}H_{22}O_{11}$, MW 342.30), trehalose-6-phosphate ($C_{12}H_{21}O_{14}P$, MW 420.26), palatinose hydrate ($C_{12}H_{22}O_{11}$, MW 342.30), and thiodiglucoside ($C_{12}H_{22}O_{10}S$, MW 358.36) from the left to the right and from the upper to the bottom (herein, the formulas and the molecular weights of all the compounds are respectively shown under the structures thereof, as shown in FIG. 1). The aforementioned compounds were used to test for their potentials to reduce the ATXN3/$Q_{75}$ aggregation.

[ATXN3 cDNA Constructs]

Polyadenylated RNA (200 ng) isolated from neuroblastoma SK-N-SH cells was reverse transcribed using the SuperScript™ III reverse transcriptase (Invitrogen). The sense and antisense primers used for ATXN3/$Q_{14}$ cDNA (+826~+1152, NM_004993) amplification were 5'-ATTCAGCTAAGT<u>ATG</u>CAAGGTAGTTCCA (codon for Met257 underlined, SEQ ID NO: 1) and 5'-CATG<u>CCATGG</u>CATGTTTTTTTCCTTCTGTT (NcoI site underlined, SEQ ID NO: 2). The amplified 3' polyQ-containing cDNA fragment (translated into amino acids 257~361) was cloned into pGEM-T Easy (Promega) and sequenced. The ATXN3/$Q_{14}$ cDNA was excised with EcoRI (in pGEM-T Easy vector) and NcoI and subcloned into pEGFP-N1 (Clontech). Then, DNA fragment containing in-frame ATXN3/$Q_{14}$-EGFP was excised with HindIII-NotI and subcloned into the pcDNA5/FRT/TO (Invitrogen). The ATXN3/$Q_{75}$ cDNA was made by replacing an 88 bp ATXN3/$Q_{14}$ BsmBI-BsmFI fragment with a 271 bp ATXN3/$Q_{75}$ fragment from the cDNA clone of a SCA3 patient.

[Flp-In 293 ATXN3 Cell Lines and SH-SY5Y TBP Cell Lines]

The cloned pcDNA5/FRT/TO-nTBP/$Q_{36\sim79}$-GFP plasmids were used to generate the isogenic TBP cell lines by targeting insertion into Flp-In SH-SY5Y cells. The cloned plasmids and pOG44 (Invitrogen) plasmids for expression Flp recombinase were co-transfected into the aforementioned SH-SY5Y host cell lines by using the liposome-mediated transfection (LF2000, Invitrogen). In addition, the cloned pcDNA5/FRT/TO-ATXN3/$Q_{14}$ and $Q_{75}$ plasmids were used to generate the isogenic ATXN3/$Q_{14\sim75}$ cell lines by targeting insertion into Flp-In™ 293 cells. The aforementioned cell lines were grown in medium containing 5 μg/mL blasticidin and 100 μg/mL hygromycin (InvivoGen).

[ATXN3/$Q_{75}$ and TBP/$Q_{79}$ Aggregation Assay]

293 ATXN3/$Q_{75}$-GFP cells were plated into 96-well ($2\times10^4$/well) dishes, grown for 24 hr and treated with different concentrations of the trehalose or analogs (100 nM~100 μM) and suberoylanilide hydroxamic acid (SAHA, Cayman Chemical) for 8 hr. Then, doxycycline (10 μg/mL, BD) was added to the medium in each well to induce ATXN3/$Q_{75}$-GFP expression for 6 days. Oxaliplatin (5 μM, Sigma) was also added to increase aggregate accumulation through inhibition of cell division. Then, cells were stained with Hoechst 33342 (0.1 μg/mL, Sigma) and aggregation percentage was assessed by high content analysis (HCA) system (ImageXpressMICRO, Molecular Devices), with excitation/emission wavelengths at 482/536 (EGFP).

SH-SY5Y TBP/$Q_{79}$-GFP cells were seeded in 6-well ($2\times10^5$/well) plate, with all trans-retinoic acid (10 μM, Sigma) added at seeding time. At day 2, cells were treated with trehalose or analogs (10 μM) for 8 hr. Then doxycycline (5 μg/mL) was added and the cells were kept in the medium containing 10 μM trans retinoic acid, doxycycline and trehalose/analogs for 7 days. After that, cells were stained with Hoechst 33342 (0.1 μg/mL) and aggregation percentage was assessed by HCA.

[Hydrolysis of Trehalose and Analogs)

Hydrolysis of trehalose and analogs was tested using porcine kidney trehalase (Sigma-Aldrich, T8778). The standard reaction was performed by adding 0.001 unit of trehalase into 50 μl reaction solution containing 135 mM citric acid (pH 5.7) and 28 mM trehalose or trehalose analogs. In addition, the inhibition of analog against the trehalase activity was also examined. The standard reaction was performed by adding 0.001 unit of trehalase into 50 μl reaction solution containing 135 mM citric acid (pH 5.7) and 44.8 mM α-D-lactulose, 44.8 mM α-D-melibiose, 0.2 μM validamycin A, or 0.2 μM validoxylamine A. Trehalase was incubated with analog for 30 min at 37° C., and the reaction was then started by addition of trehalose. After incubation at 37° C. for 2 hr, the reaction was terminated by heating the mixture in boiling water for 15 min. The activity of trehalase was assayed by measuring the amount of glucose produced from trehalose. The amount of carbohydrates after each enzymatic reaction was measured using a high-performance liquid chromatography (HPLC) system (Schambeck SFD 2100) equipped with an refractive index (RI) detector (SFD, RI 2000) at a flow rate of 1 ml/min. A carbohydrate analysis column (Shodex SUGAR SZ5532, 6.0 mm ID×150 mm L) equilibrated with 75% acetonitrile, 24% Milli-Q water, and 1% formic acid was used. The RI detector and column oven temperature were set to 40 and 60° C., respectively.

[Flp-In 293 DsRed-LC3 Cells and Autophagy Assay]

The pDsRed-LC3 construct encoding human microtubule-associated protein 1 light chain 3 beta (MAP1LC3B, NM_022818) was generated by PCR amplification of LC3 coding sequence from human cDNA using the forward (5'-AAGCTTCCATGCCGTCGGAGAAG, HindIII site underlined, SEQ ID NO: 3) and reverse (5'-TTTTACACTGACAATTTCATC, SEQ ID NO: 4) primers. The amplified LC3 cDNA was cloned into pGEM-T Easy (Promega) and sequenced. The LC3 cDNA was excised with HindIII and EcoRI (in pGEM-T Easy) restriction enzymes and subcloned into the corresponding sites of pDsRed-Monomer-C1 (Clontech). Then, AgeI (blunted)-BamHI (in pDsRed-Monomer-C1) DNA fragment containing in-frame DsRed-LC3 was ligated with BamHI-AhdI (997~4215) and AhdI-EcoRV (4215~1032) fragments of pcDNA5/FRT/TO (Invitrogen). The Flp-In DsRed-LC3 cells were generated using the resulting plasmid according to the supplier's instructions (Invitrogen) and maintained in medium containing 5 μg/mL blasticidin and 100 μg/mL hygromycin (InvivoGen).

For examining autophagy activity induced by trehalose and analogs, the DsRed-LC3 cells ($10^6$) were transfected using T-Pro reagent (JF Biotechnology) with ATXN3/$Q_{75}$ plasmid (5 μg). After 24 hr, the transfected cells were plated into 96-well ($2\times10^4$/well) dishes, grown for 20 hr, and treated with trehalose, lactulose or melibiose (10~50 μM) for 8 hr. Then doxycycline (10 μg/mL) was added to the medium to induce DsRed-LC3 and ATXN3/$Q_{75}$ expression for 6 days and punta within cells was analyzed by using HCA system, with excitation/emission wavelengths at 562/624 nm.

[Western Blot Analysis]

Total proteins were prepared using lysis buffer containing 5% glycerol, 0.5% Triton X-100, 1 mM dithiothreitol, and protease inhibitor cocktail (Sigma). Proteins (20 μg) were separated on 10% SDS-polyacrylamide gel electrophoresis and blotted on to nitrocellulose membranes by reverse electrophoresis. After blocking, the membrane was probed with GFP (1:500 dilution, Santa Cruz), LC3 (1:3000 dilution, MBL International), β-actin (1:5000 dilution, Millipore) or GAPDH (1:1000 dilution, MDBio) at 4° C. overnight. Then the immune complexes were detected by horseradish peroxidase-conjugated goat anti-mouse or goat anti-rabbit IgG antibody (1:5000 dilution, GeneTex) and chemiluminescent substrate (Millipore).

[Organotypic Cerebellar Slice Culture and Immunostaining]

Whole brain were isolated from p7 SCA17 mice and transferred to ice-cold culture medium containing 50% Basal Medium Eagle (Invitrogen), 25% Hank's buffered salt solution (Invitrogen), 25% horse serum (Invitrogen), 0.5% D-glucose (Sigma), 1 mM GlutaMAX-I (Invitrogen), 100 U/ml penicillin (Invitrogen) and 100 μg/ml streptomycin (Invitrogen). The cerebellum was separated from the other brain regions in ice-cold medium, and the hemisphere was then cut into 350 μm parasagittal sections with a vibratome (VT1200S, Leica). To improve the survival rate of cerebellar slices, we continuously bubbled the medium with 95% $O_2$ and 5% $CO_2$ during the sectioning. The slices were then cultured on 0.4 μm pore size culture plate inserts (Millipore) in six-well plates. All treatments were applied to the slices at day 2. After culture for 7 days, cells were immunostained with primary antibody [IP3R-1 (for Purkinje cells), 1:1000, Santa Cruz; 1TBP18 (for aggregation), 1:30000, QED Bioscience], fluorescence-conjugated secondary antibody (1:500, Invitrogen) and DAPI (1:10000, Sigma). The staining results were observed by confocal microscope (DMRE, TCS SP2, Leica).

[Statistical Analysis]

For each set of values, data were expressed as the means±standard deviation (SD). Three independent experiments were performed and non-categorical variables were compared using the Student's t-test. All P-values were two-tailed, with values of P<0.05 considered significant.

[Results]

[Construction of 293 Cells Expressing ATXN3/$Q_{75}$ Aggregates]

Figure 2:
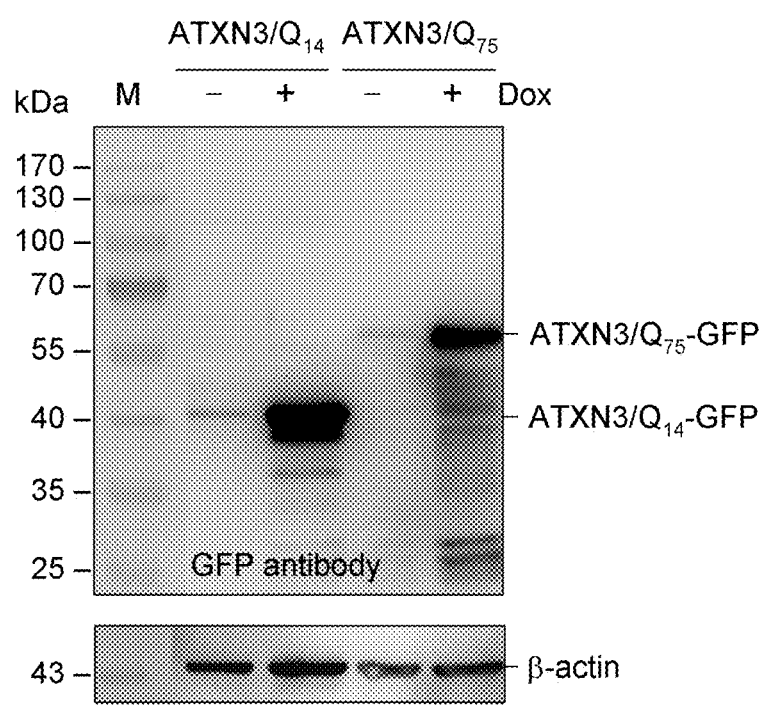
FIG. 2 shows a result of Western blot analysis of ATXN3/$Q_{14-75}$-GFP protein expression induced with doxycycline according to one preferred embodiment of the present invention.

In the present example, GFP-tagged ATXN3 C-terminal $Q_{14-75}$-containing fragment was cloned to establish Flp-In 293 cells with ATXN3/$Q_{14-75}$-GFP expression in an inducible fashion, wherein ATXN3/$Q_{14}$ was used as a control. As shown in FIG. 2, the GFP antibody detected 40 kDa ATXN3/$Q_{14}$-GFP and 57 kDa ATXN3/$Q_{75}$-GFP proteins in doxycycline (Dox) induced ATXN3 cells.

[Effect of Trehalose and Analogs on ATXN3/$Q_{75}$ Aggregation in Flp-In 293 Cell Model]

Figure 3:
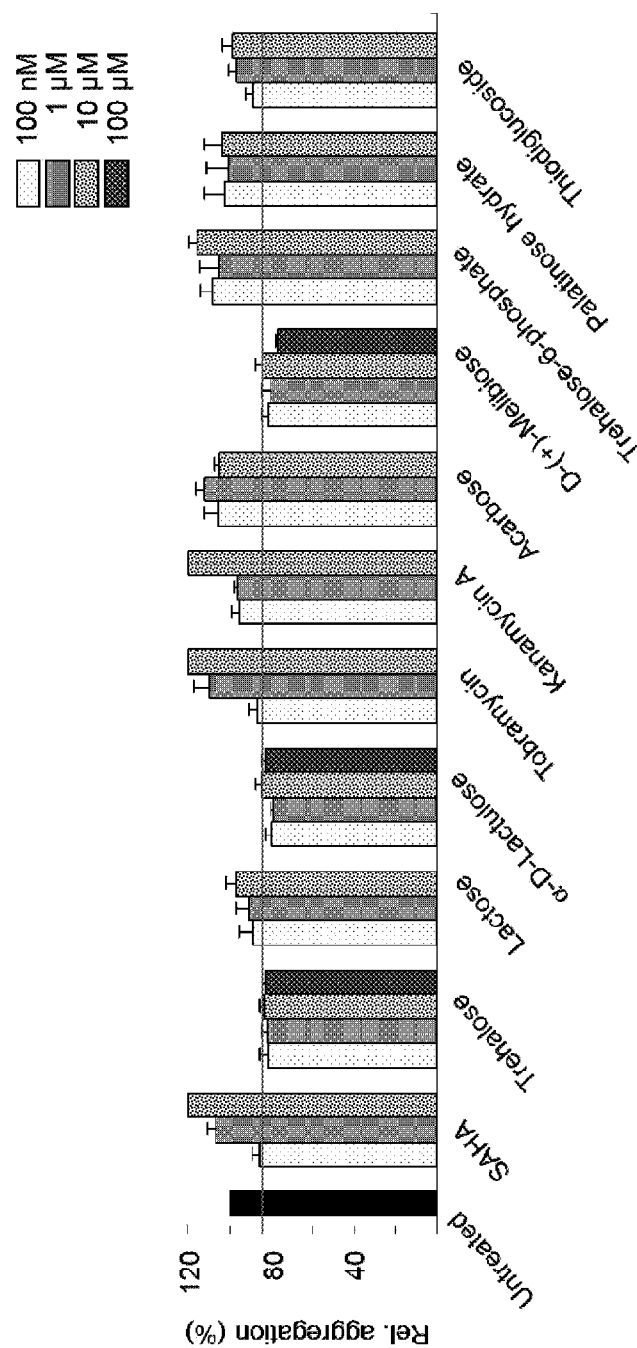
FIG. 3 shows a result of polyQ aggregation analysis of ATXN3/$Q_{14-75}$-GFP cells treated with the trehalose and analogs according to one preferred embodiment of the present invention.

In the present example, the influences of the trehalose and analogs and HDAC inhibitor SAHA in the ATXN3/$Q_{75}$-GFP cells were respectively examined. After 6 days of the treatment of doxycycline and oxaliplatin, the fluorescence microscopy images were observed, and aggregation percentage of ATXN3/$Q_{75}$-GFP cells was assessed by high-content analysis system. The result was shown in FIG. 3, as a positive control, HDAC inhibitor SAHA reduced the ATXN3/$Q_{75}$ aggregation to 85% (at 100 nM) as compared to untreated cells (100%). The tested trehalose, lactulose and melibiose displayed good aggregation-inhibitory potential (77~85%) at 100 nM~100 μM.

[Hydrolysis of Trehalose and Analogs by Trehalase and Inhibition of Analogs Against Trehalase]

Figure 4A:
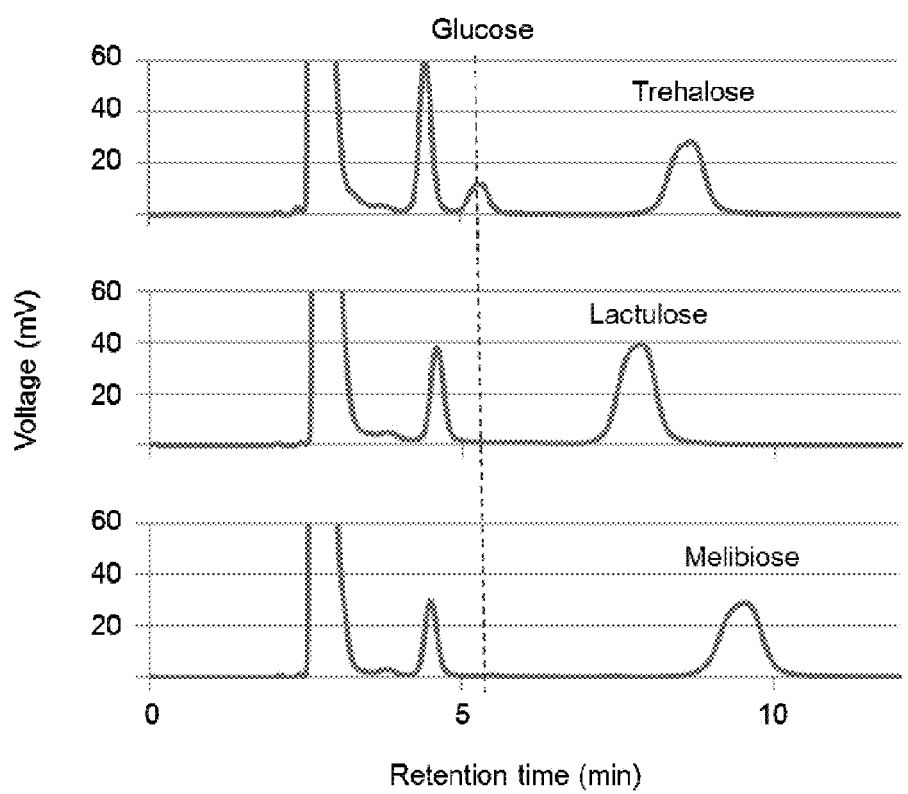
FIG. 4A shows an analysis result of the hydrolysis of the trehalose and analogs according to one preferred embodiment of the present invention.
Figure 4B:
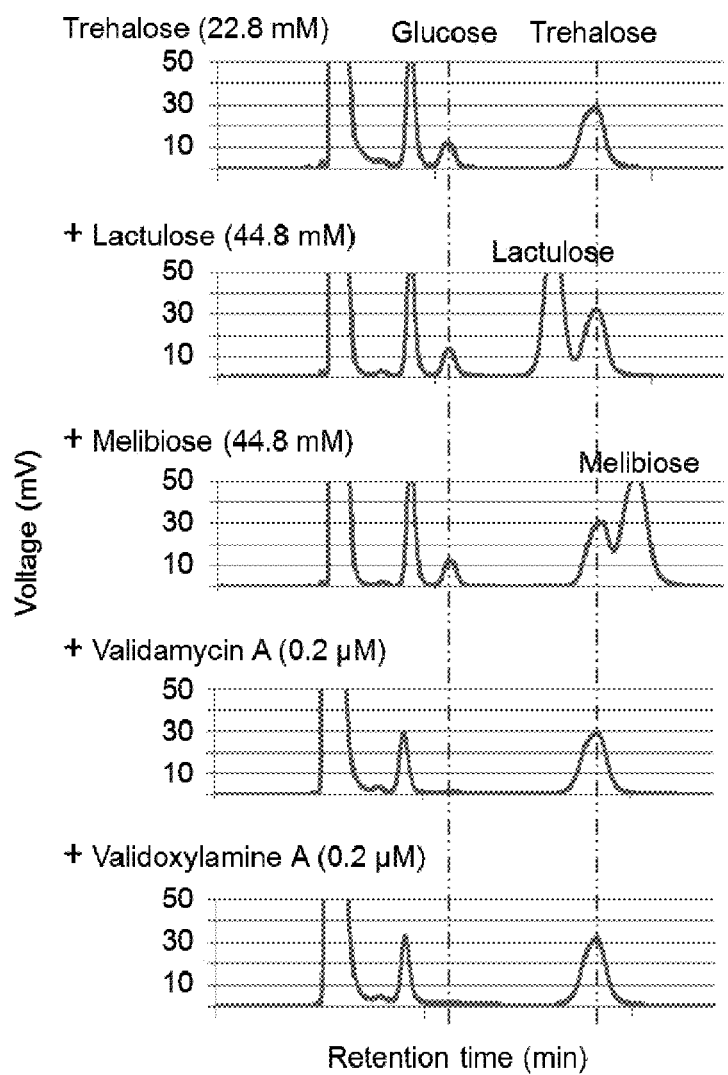
FIG. 4B shows an analysis result of the inhibition of the trehalose hydrolysis by validamycin A and validoxylamine A according to one preferred embodiment of the present invention.

Hydrolysis of trehalose, lactulose and melibiose (28 mM) was tested using porcine kidney trehalase (1 mU). As shown in FIG. 4A, while trehalose was readily digested by trehalase, no smaller carbohydrates, such as glucose, fructose, or galactose, were observed with the addition of lactulose or melibiose. This implys that lactulose and melibiose could not be hydrolyzed by trehalase. In addition, as shown in FIG. 4B, the amount of glucose generated from trehalose with the addition of lactulose or melibiose was similar to that with the addition of trehalose only, implying that the addition of lactulose or melibiose did not inhibit the trehalase activity. Furthermore, there were no peaks represented glucose observed with the addition of trehalase inhibitor validamycin A or validoxylamine A, implying that the addition of validamycin A or validoxylamine A can inhibit the trehalase activity for digesting trehalose into glucose.

[Effect of Trehalose, Lactulose and Melibiose on Autophagy Activation]

Figure 5A:
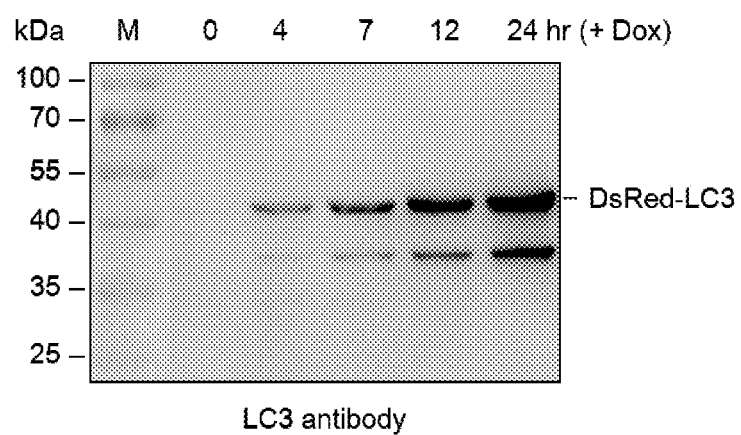
FIG. 5A shows a result of Western blot analysis of DsRed-LC3 protein expression induced with doxycycline according to one preferred embodiment of the present invention.
Figure 5B:
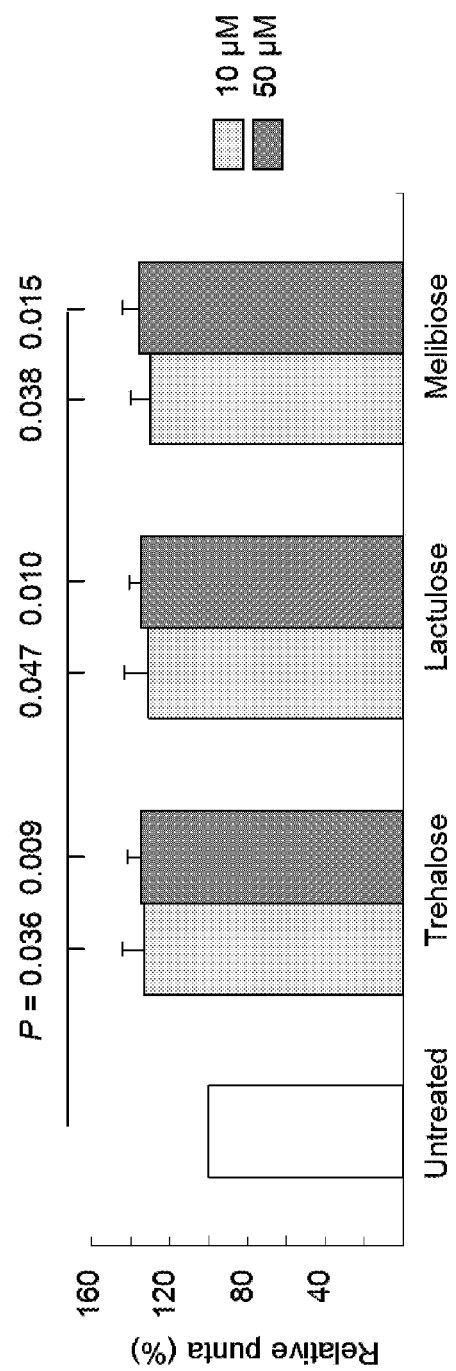
FIG. 5B shows an analysis result of the autophagy activation of Flp-In 293 DsRed-LC3 cells treated with the trehalose and analogs according to one preferred embodiment of the present invention.
Figure 5C:
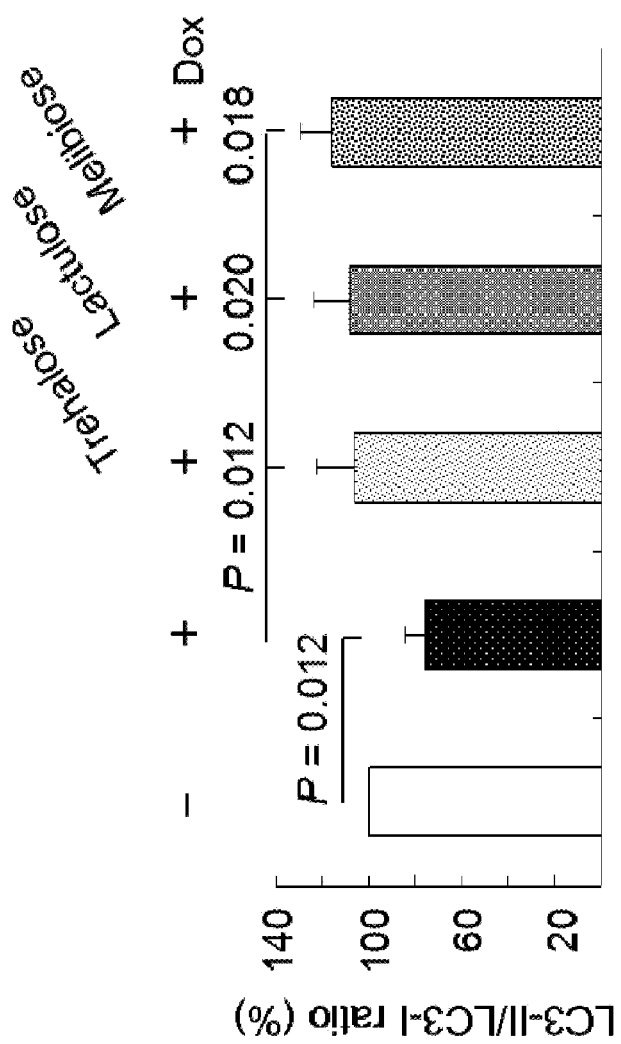
FIG. 5C shows a result presenting the LC3-II/LC3-I ratio in Flp-In 293 DsRed-LC3 cells treated with the trehalose and analogs according to one preferred embodiment of the present invention.

To test trehalose and analogs potentially enhancing autophagy activity, we established a 293-based fluorescent reporter cell model with induced DsRed-LC3 expression. As shown in FIG. 5A, the LC3 antibody detected a 42 kDa DsRed-LC3 protein in doxycycline (+Dox) induced cells. The Flp-In cells were transfected with ATXN3/$Q_{75}$ plasmid for 24 hr, treated with trehalose, lactulose or melibiose (10~50 μM) for 8 hr and induced DsRed-LC3 expression. Frequency of cells exhibiting DsRed-LC3-positive vacuoles (punta) was quantified as indicative of autophagosome formation. As shown in FIG. 5B, treatment of trehalose, lactulose and melibiose significantly (130%~136%, P=0.047~0.009) induced the recruitment of DsRed-LC3 to autophagic vacuole. To examine if trehalose and analogs also induced autophagy in induced ATXN3/$Q_{75}$ 293 cells, we compared the expression levels of lipid phosphatidylethanolamine (PE)-conjugated LC3-II and cytosolic LC3-I between with and without trehalose/analogs and/or Dox treatment, as LC3-II is the only known protein that specifically associates with autophagosomes and not with other vesicular structures. As shown in FIG. 5C, induced expression of ATXN3/$Q_{75}$ (+Dox) for 6 days attenuated the LC3-II/LC3-I ratio (76%, P=0.012). This reduction can be rescued by the addition of trehalose, lactulose or melibiose (10 μM), with significantly increased LC3-II/LC3-I ratio (106%~116%, P=0.020~0.012). These findings indicated that trehalose and analogs enhanced autophagy activity on 293 ATXN3/$Q_{75}$ cell model.

[Effect of Trehalose, Lactulose and Melibiose on SH-SY5Y TBP/$Q_{79}$]

Figure 6:
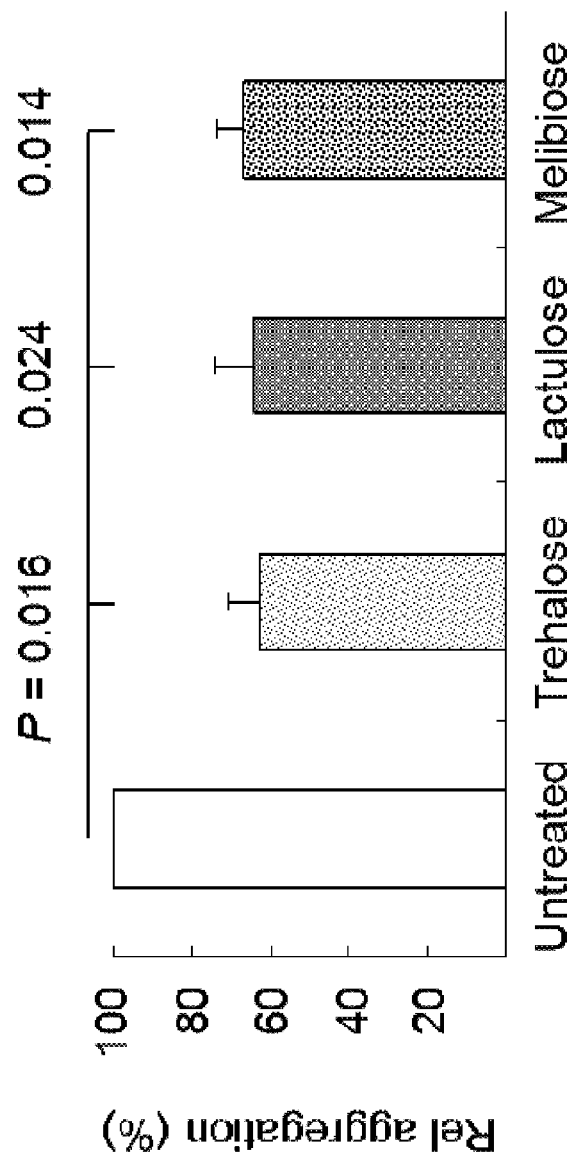
FIG. 6 shows a result of polyQ aggregation analysis of SH-SY5Y TBP/$Q_{79}$ cells treated with the trehalose and analogs according to one preferred embodiment of the present invention.

To test the aggregation reduction potential of trehalose and analogs in neuronal cells, we constructed Flp-In SH-SY5Y SCA17 cells with N-terminal TBP/$Q_{79}$-GFP expression in an inducible fashion. When TBP/$Q_{79}$ SH-SY5Y cells were differentiated for 7 days using retinoic acid, aggregates were seen in about 2% TBP/$Q_{79}$-GFP cells (not shown in the figure) under a microscope. The SH-SY5Y TBP/$Q_{79}$-GFP cells were used to examine if trehalose and analogs reduce aggregation. As shown in FIG. 6, treatment of 10 μM trehalose, lactulose or melibiose leaded to 38%~33% of aggregation reduction (P=0.024~0.014) in TBP/$Q_{79}$ expressed differentiated neuronal cells. These findings indicated that trehalose, lactulose and melibiose reduce TBP/$Q_{79}$ aggregation in differentiated neuronal cell model.

[Effect of Trehalose, Lactulose and Melibiose on Purkinje Cell Aggregation in SCA17 Mouse Cerebellar Slice Culture]

Figure 7:
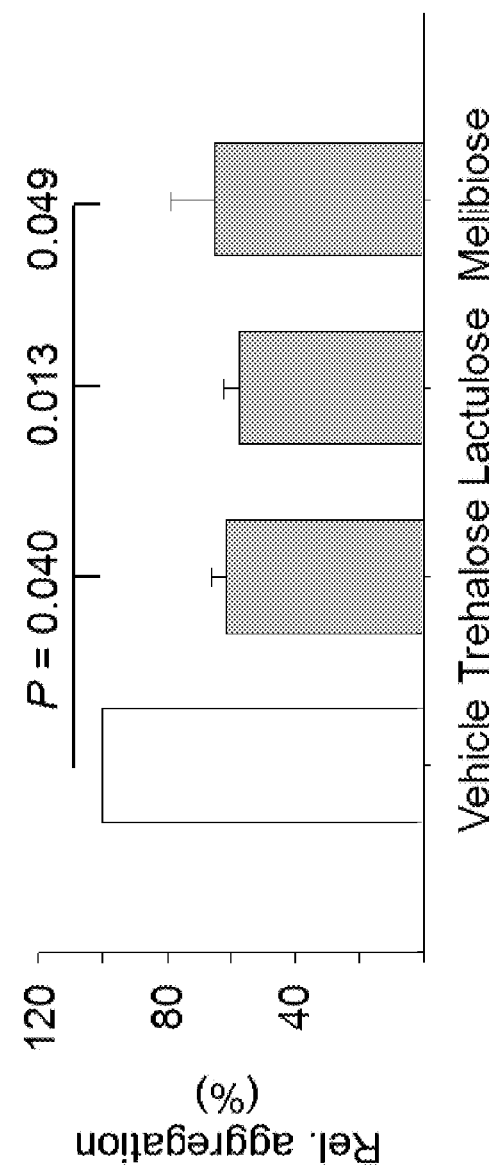
FIG. 7 shows a result of polyQ aggregation analysis in SCA17 mouse cerebellar slice culture treated with the trehalose and analogs according to one preferred embodiment of the present invention.

We tested the aggregation reduction potential of trehalose and analogs (100 μM for 6 days) in SCA17 mouse cerebellar slice culture. The quantitative results of treatment are shown in FIG. 7. Trehalose, lactulose and melibiose reduced the Purkinje cell aggregation significantly (65%~57%, P=0.049~0.013).

Although the present invention has been explained in relation to its preferred embodiment, it is to be understood that many other possible modifications and variations can be made without departing from the spirit and scope of the invention as hereinafter claimed.

What is claimed is:

1. A method for treating an abnormal polyglutamine-mediated disease, comprising:

administering a pharmaceutical composition comprising a trehalose-based compound to a subject in need thereof, wherein the trehalose-based compound is selected from the consisting of a compound of the following formula 1, a compound of the following formula 2, a compound of the following formula 3, and derivatives thereof:

[Formula 1]

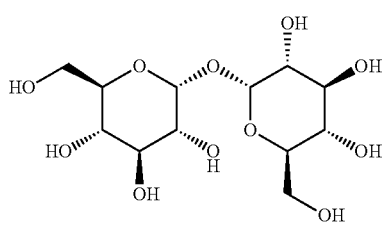

[Formula 2]

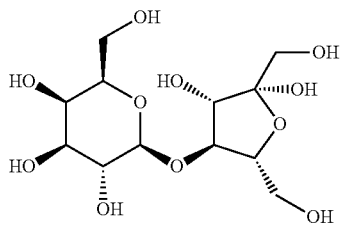

[Formula 3]

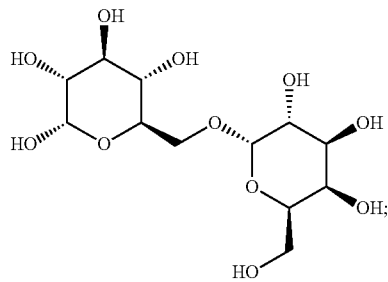

wherein the abnormal polyglutamine-mediated disease is selected from the group consisting of spinocerebellar ataxia types 1, 2, 3, 6, 7, 8, and 17, and dentatorubropallidoluysian atrophy (DRPLA).

2. The method as claimed in claim 1, wherein a concentration of the trehalose-based compound is in a range from 50 nM to 200 μM based on a total weight of the pharmaceutical composition.

3. The method as claimed in claim 2, wherein the concentration of the trehalose-based compound is in a range from 100 nM to 100 μM based on a total weight of the pharmaceutical composition.

4. The method as claimed in claim 1, wherein the pharmaceutical composition further comprises: a trehalase inhibitor.

5. The method as claimed in claim 4, wherein the trehalase inhibitor is validamycin A, validoxylamine A, trehazolin, MDL 25637, castanospermine, deoxynojirimycin, 1-thiatrehazolin, salbostatin or calystegin B4.

6. The method as claimed in claim 1, wherein the pharmaceutical composition suppresses polyglutamine aggregation through enhancing autophagy activity in the subject in need.

7. The method as claimed in claim 6, wherein the pharmaceutical composition increases a ratio of LC3-II to LC3-I (LC3-II/LC3-I) to enhance the autophagy activity in the subject in need.

* * * * *